US00PP10050P

United States Patent [19]

Bergman

[11] Patent Number: Plant 10,050

[45] Date of Patent: Oct. 7, 1997

[54] AZALEA PLANT NAMED 'PARTY FAVOR'

[75] Inventor: Wendy R. Bergman, Lehigh Acres, Fla.

[73] Assignee: Yoder Brothers, Inc., Barberton, Ohio

[21] Appl. No.: 636,482

[22] Filed: Apr. 12, 1996

[51] Int. Cl.[6] ..... A01H 5/00

[52] U.S. Cl. ..... Plt./56

[58] Field of Search ..... Plt./56, 57, 55

*Primary Examiner*—James R. Feyrer
*Assistant Examiner*—Kent L. Bell
*Attorney, Agent, or Firm*—Foley & Lardner

[57] ABSTRACT

An azalea plant named Party Favor particularly characterized by its evergreen foliage, semi-double flower form, bright dark pink flower color, ease of budding, uniform plant habit and flowering response in a year round controlled program and by its excellent cooler tolerance, and good keeping quality.

1 Drawing Sheet

The present invention comprises a new and distinct cultivar of Azalea, a greenhouse forcing type, hereinafter referred to as Party Favor.

Party Favor, identified as Code 1013 during the selection process, originated from a planned cross hybridization between two selected breeding lines in a controlled breeding program in Fort Myers, Fla.

The female, or seed parent of Party Favor is a seedling known as Code 196, a proprietary breeding line. The male, or pollen parent is a seedling known as Code 227, also a proprietary breeding line.

Party Favor was discovered and selected by Wendy R. Bergman as one flowering plant within the progeny of the stated cross in January 1992, in Fort Myers, Fla.

The first asexual reproduction of Party Favor was accomplished when vegetative cuttings were taken from the initial selection in April 1992, in Fort Myers, Fla., by technicians working under formulations established and supervised by Wendy R. Bergman.

Horticultural examination of controlled flowerings of successive generations of plants derived from cuttings taken from the original selection has shown that the unique combination of characteristics as herein disclosed for Party Favor are fixed and retained through successive generations of asexual reproduction.

Party Favor has not been observed under all possible environmental conditions. The phenotype may vary significantly with variations in environment such as temperature, light intensity and day length, without, however, any variance in the genotype.

The following observations, measurements and comparisons describe plants that were grown in Fort Myers, Fla. in a controlled greenhouse environment and following a commercial schedule.

The following traits have been repeatedly observed and are determined to be basic characteristics of Party Favor, which, in combination, distinguish this azalea as a new and distinct cultivar:

1. Dark pink flower color (66C), with a fuchsia blotch.
2. Semi-double flower form.
3. The flowers range in size from 8.0 to 9.5 cm in diameter with 8.7 cm the average size.
4. Compact, uniform and dense plant habit.
5. Fast, uniform response in year round controlled flowering programs, forcing in 22 days on average.
6. Good longevity in a simulated home environment, with flowers lasting up to 26 days.
7. Excellent foliage retention and no flower bud damage when cooled for 6 weeks with no lighting at 38° F.

The accompanying color photograph shows in perspective view the unique features of the new cultivar, with colors being as true as possible with color illustrations of this type.

Of the commercial cultivars known to the inventor, the most similar in comparison to Party Favor is Solitaire disclosed in U.S. Plant Pat. No. 3,171. Party Favor is similar to Solitaire in that both are pink evergreen azaleas suitable for greenhouse forcing.

Party Favor differs from Solitaire in that Party Favor's flowres are darker pink and display a distinct fuchsia blotch. The plant habit of Party Favor is much more dense and heavily branched than that of Solitaire.

In the following description color references are made to The Royal Horticultural Society Colour Chart. The color values were determined on Mar. 13, 1995. All readings were taken in an office under cool white fluorescent lights, facing a west window between the hours of 10:00 a.m. and 2:00 p.m.

Classification:

*Botanical.*—*Rhododendron hybrida*, evergreen type.

*Commercial.*—Florist forcing pot azalea, cv. Party Favor.

Inflorescence

Flower (general):

*size.*—8.0 to 9.5 cm.

*Borne.*—Terminal cluster, usually three (3) per bud, ranging from two to four (2–4). Occasionally more than one bud per stem.

*Form.*—Semi-double. Funnel-form.

*Blooming habit.*—Once profusely. Buds easily and uniformly in a year round flowering program. The majority of terminal buds break color within one (1) week of the first. Flowering begins approximately 22 days after the start of forcing.

*Fragrance.*—Present.

Corolla (petals):

*Texture.*—Soft.

*Substance.*—Heavy.

*Shape.*—Rounded with slightly undulate margin.

*Color (fully open).*—Generally 66C, bright dark pink. Upper surface: Edge: 66C. Center: 66C. Base: 66D. Lower surface: 67D. Blotch: 61C.

Bud:

*Size.*—Medium.

*Shape.*—Conoidal.

*Color.*—67C.

*Bud sheath.*—Medium brown with light brown hairs.

Calyx:

*Forms.*—Enlarged and somewhat transformed into petals, shape irregular, varying from 1.0–4.5 cm long.

*Color.*—66C and 143B. Lower surface: 67D and 143B.

Peduncle:

*Length.*—1.0–2.0 cm.

*Strength.*—Strong.

*Aspect.*—Pubescent.

Reproductive organs:

*Androecium* (*stamens*).—Number: Zero to five (0–5). Many are petaloid. Anthers: 183D. Filaments: Length: 2.5–4.0 cm. Color: Between 73B and 73C.

*Gynoecium* (*pistil*).—Stigma: 38A. Style: Length: 3.0–5.0 cm. Color: Between 52B and 52C. Ovary: Pubescent.

Plant Characteristics

Foliage:

*Type.*—Evergreen.

*Arrangement.*—Alternate.

*Shape.*—Elliptic.

*Size.*—Length: 2.0–8.5 cm. Width: 0.8–3.5 cm.

*Margin.*—Entire.

*Color.*—Immature: Upper surface: 144A. Lower surface: 145B. Mature: Upper surface: 139A. Lower surface: 146B. Texture: Leathery. Tomentum: Present on upper surface. Insignificant.

Stems:

*Color.*—Immature: 181D. Mature: 165B. Tomentum: Little present, light brown. Insignificant.

Plant habit: Compact, semi-upright, dense bush which is uniform and symmetrical in a six-inch (6") pot when pinched three (3) times. Total crop time to the dormant budded stage is 40–42 weeks to produce a plant approximately 30 cm in diameter and having a total height of 30–36 cm. Internode lengths vary widely from 2–25 mm on the same stem.

Branching habit: Free branching, producing three to five (3–5) breaks when a vegetative cutting is pinched.

Rooting: Roots easily in eight to ten (8–10) weeks with 75° F. soil temperature.

Budding ease: Plants produce flower buds easily and uniformly year round with the use of commercially available plant growth regulators. Natural season response has not been ascertained.

Cooler tolerance: Plants placed in a cooler as a means of breaking dormancy perform very well. Party Favor is tolerant of six (6) weeks in an unlighted cooler without excessive bud damage or foliage loss.

Blooming: Plants reach the stage of 12 buds showing color in 22 days on average after the cooling treatment. This varies from 17 to 28 days depending upon time of year. Party Favor flowers uniformly and profusely across the plant.

Shelf life: When plants are moved to an office or home environment at the stage of eight (8) open flowers, they maintain an attractive appearance for 24 days on average.

It is claimed:

1. A new and distinct cultivar of azalea named Party Favor, as described and illustrated.

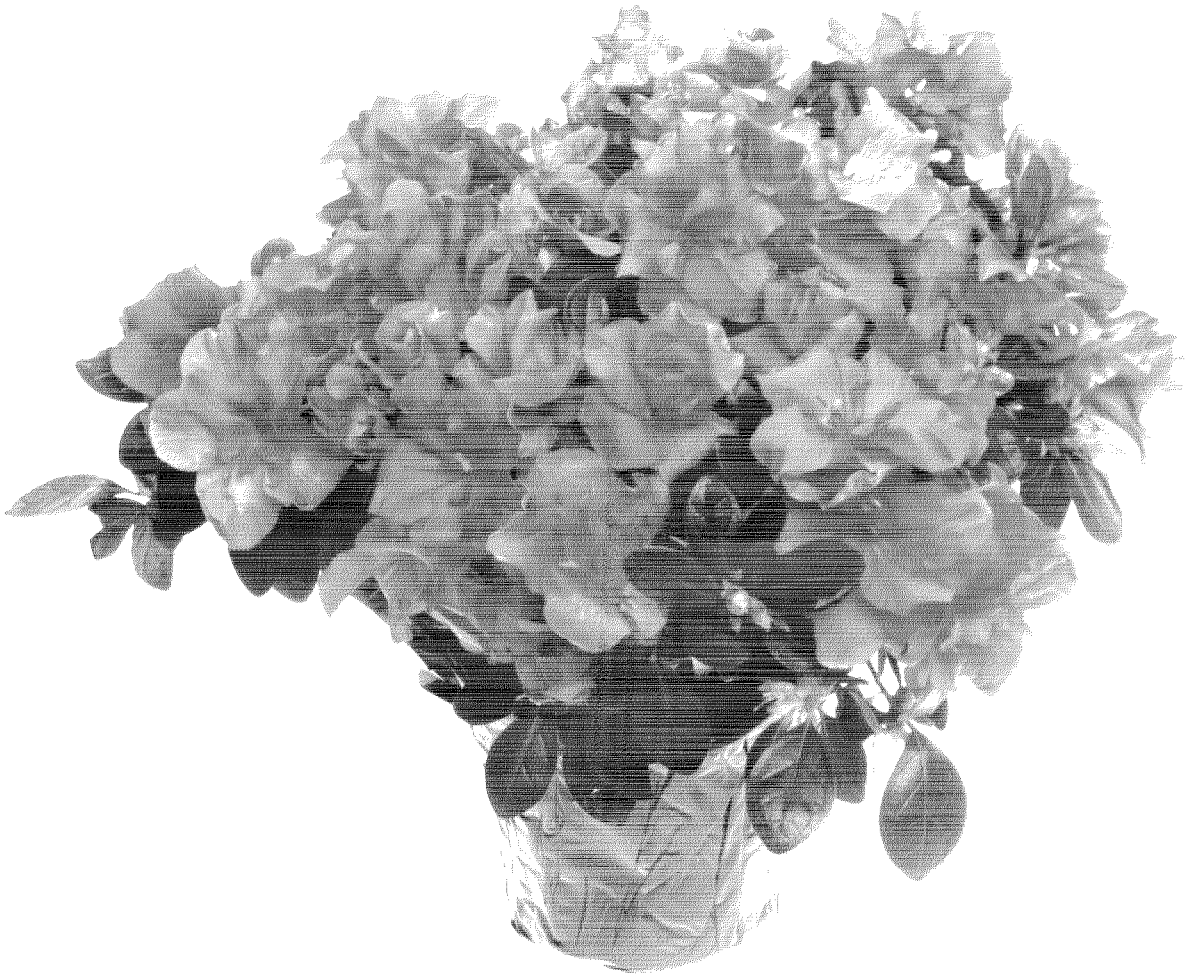

* * * * *